United States Patent [19]
Hart et al.

[11] Patent Number: 5,853,374
[45] Date of Patent: Dec. 29, 1998

[54] TISSUE COLLECTION AND RETRIEVAL BAG

[75] Inventors: Charles C. Hart, Huntington Beach, Calif.; Desmond H. Birkett, Boston, Mass.

[73] Assignee: Applied Medical Resources Corporation, Laguna Hills, Calif.

[21] Appl. No.: 540,795

[22] Filed: Oct. 11, 1995

[51] Int. Cl.[6] .................................................. A61B 10/00
[52] U.S. Cl. ........................................... 600/562; 606/114
[58] Field of Search ..................... 128/749, 849, 128/850; 606/110, 113, 114, 127, 128

[56] References Cited

U.S. PATENT DOCUMENTS

| | | |
|---|---|---|
| 5,143,082 | 9/1992 | Kindberg et al. . |
| 5,147,371 | 9/1992 | Washington et al. . |
| 5,176,687 | 1/1993 | Hasson et al. . |
| 5,190,555 | 3/1993 | Wetter et al. . |
| 5,190,561 | 3/1993 | Graber ..................... 606/114 |
| 5,192,284 | 3/1993 | Pleatman . |
| 5,192,286 | 3/1993 | Phan et al. ............... 606/110 |
| 5,354,303 | 10/1994 | Spaeth et al. . |
| 5,368,597 | 11/1994 | Pagedas . |
| 5,465,731 | 11/1995 | Bell et al. ................. 128/749 |
| 5,611,803 | 3/1997 | Heaven et al. ........... 606/114 |
| 5,643,283 | 7/1997 | Younker ................... 606/114 |
| 5,647,372 | 7/1997 | Tovey et al. ............. 128/749 |
| 5,681,324 | 10/1997 | Kammerer et al. ...... 606/113 |

FOREIGN PATENT DOCUMENTS

| | | |
|---|---|---|
| 9204406 | 5/1992 | WIPO . |
| 9315671 | 1/1993 | WIPO . |
| 9324063 | 5/1993 | WIPO . |

*Primary Examiner*—Max Hindenburg
*Assistant Examiner*—Pamela Wingood
*Attorney, Agent, or Firm*—Richard L. Myers

[57] ABSTRACT

A tissue collection apparatus is adapted for use in capturing and removing tissue through a hole in a body wall defining a body cavity. The apparatus includes an elongate flexible enclosure sized and configured to extend through the hole with a first end of the enclosure positioned within the body cavity and a second end of the enclosure positioned outside the body cavity. Portions of the distal end define opposing first and second edges which define an opening into the enclosure. A flap extends through the opening and distally of the apparatus to form a lip facilitating placement of tissue through the opening and into the enclosure. The coupling attaches a tension member to the enclosure along at least a point disposed not more distally than the flap. The tension member can be pulled proximally through the hole in the body wall to invert the apparatus without inverting the flap so that the flap covers the second edge of the opening in order to substantially close the opening with the tissue disposed within the enclosure. A method of use includes the steps of pulling the tension member to invert the enclosure and during the pulling step covering the opening with the flap.

20 Claims, 6 Drawing Sheets

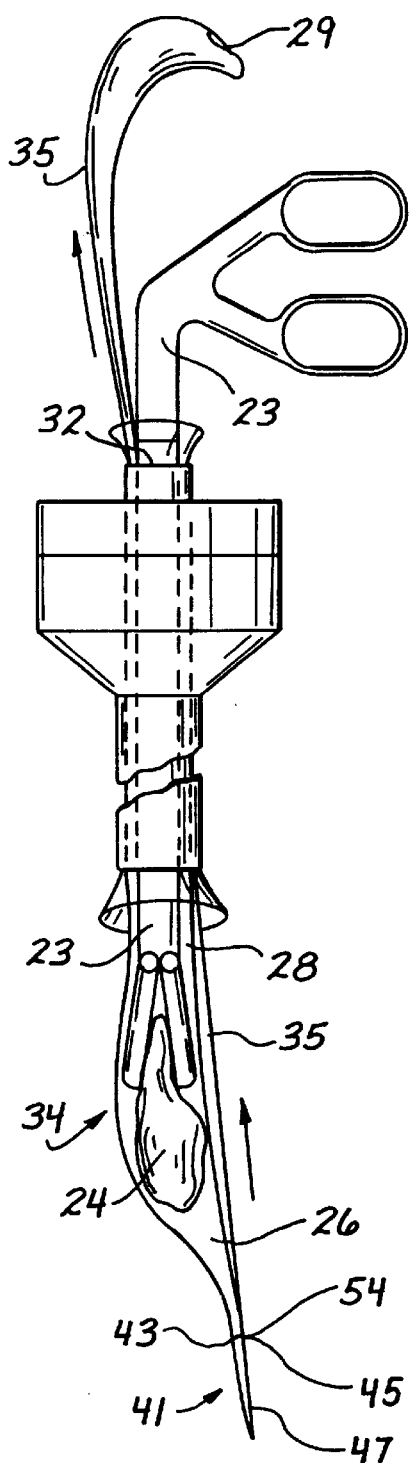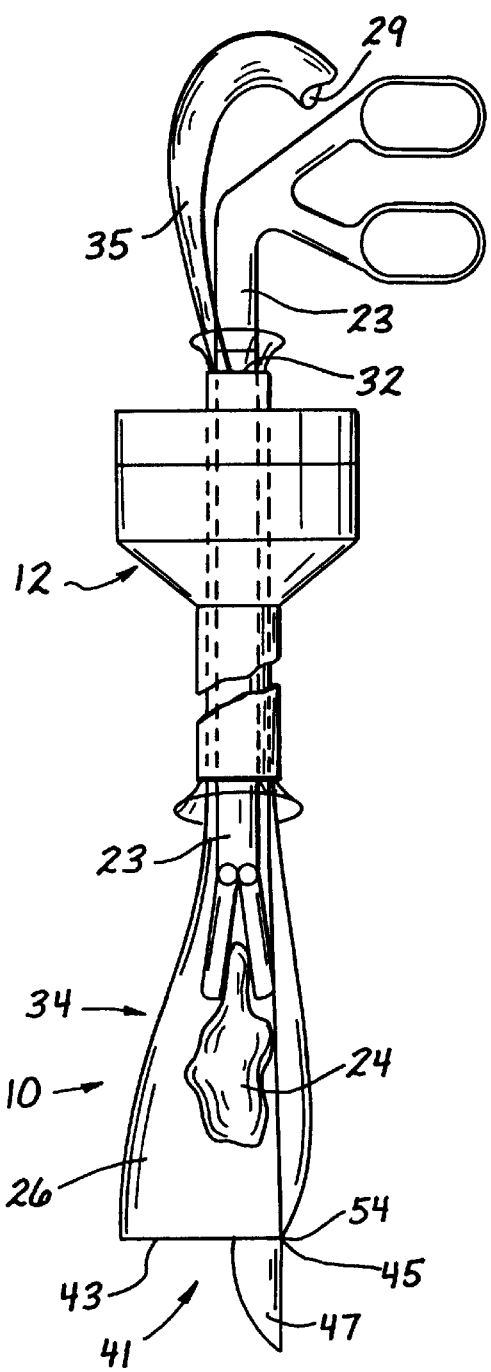
FIG. 7
FIG. 6

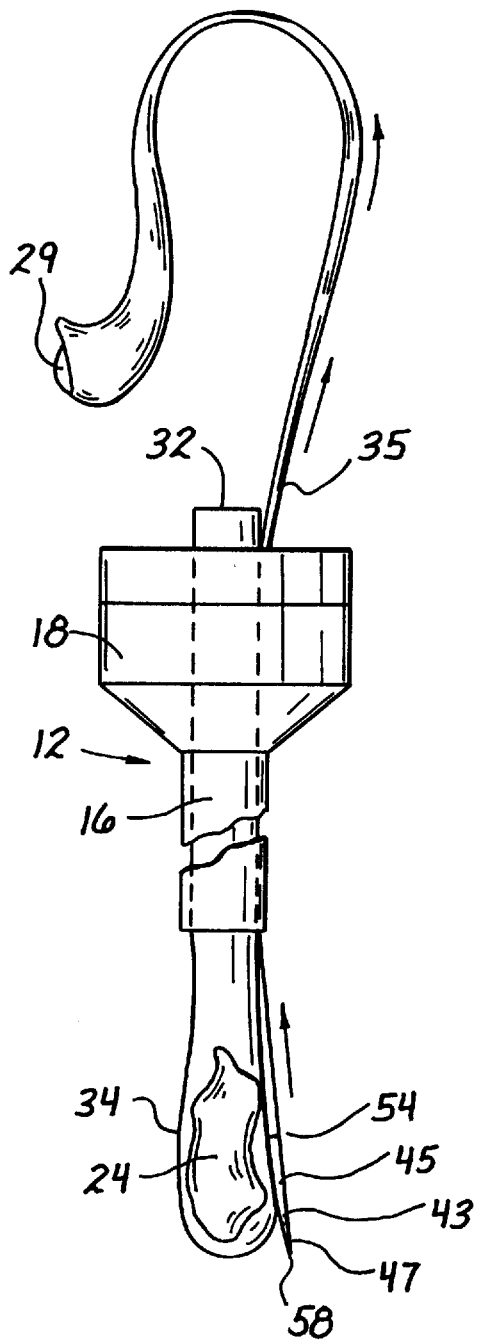
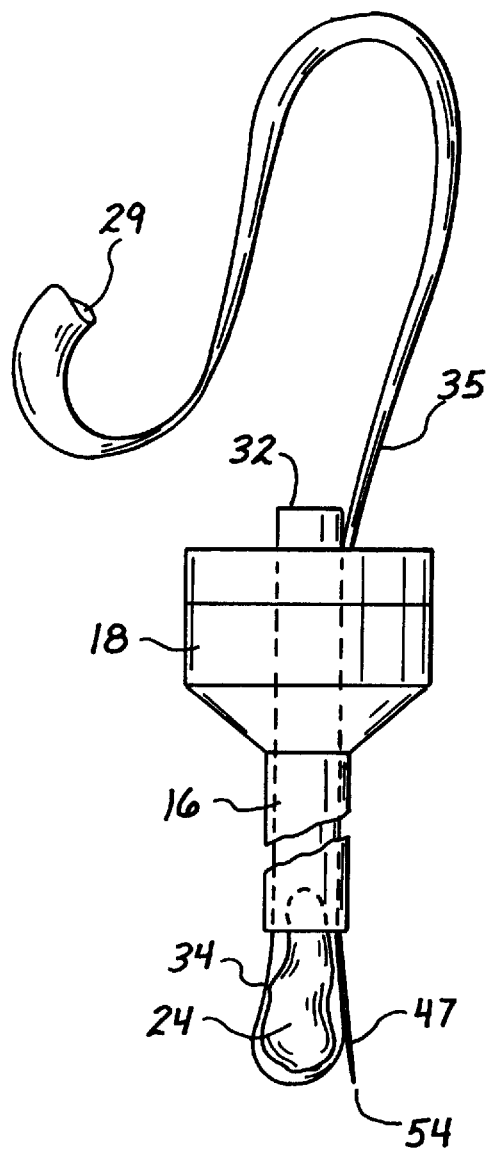
FIG. 8
FIG. 9

TISSUE COLLECTION AND RETRIEVAL BAG

BACKGROUND OF THE INVENTION

1. Field of the Invention

This invention relates generally to apparatus and methods for capturing and retrieving tissue from body cavities.

2. Discussion of the Prior Art

Laparoscopic surgery is typically performed through trocars which provide access across the abdominal wall and into the abdominal cavity. Using multiple torcars, a variety of surgical procedures can be undertaken. In many of these procedures, tissue disposed within the abdominal cavity is cut and removed from the body. Such tissue may include infected or cancerous mass, as well as blood, bile and other liquids, all referred to herein as tissue, which may pose infection problems or other complications if left within the body. It is desirable to grasp, capture and retain these materials in a bag or similar enclosure while in the body cavity, and then to remove the bag and enclosed tissue through the trocar. It is important that the containment of the tissue be accomplished as quickly as possible with minimal disturbance to the surgical site.

In the past, bags have been developed to avoid the complications associated with tissue removal in laparoscopic surgery. U.S. Pat. No. 5,176,687 issued to Hasson et al discloses a device having a membrane circumferentially and concentrically attached to a conduit with a concentric distal entryway into the membrane. The membrane is closed using a draw string, and withdrawn from the abdominal cavity.

Washington et al. in their U.S. Pat. No. 5,147,371 disclose a device having a wire forming a double loop and holding a bag at the end of a tube. The wire ends are pushed and pulled to expand and contract the radius of the loop thereby providing access to the bag. These patents and concepts are merely representative of the prior art that includes bags which can be deployed into the body cavity and manipulated with drawstrings, support rods, tubes or other closure mechanisms to close the bag prior to removal.

These devices are generally bulky and have several shortcomings. In general, they lack optimal efficiency and safety during insertion and removal of material. They are deficient in maintaining directional orientation of the bag during extracorporeal usage. They do not provide transparency which permits ease of viewing through the wall of the bag, nor do they easily accommodate a grasping instrument for placing the tissue within the bag. They do not close and seal adequately to prevent leakage, and are typically too complex and expensive for their intended purpose.

SUMMARY OF THE INVENTION

These deficiencies of the prior art are overcome with the present invention which provides a simple low cost tissue capture apparatus. The apparatus can be formed from a flexible tubular structure which is easily insertable through a trocar into a body cavity. A grasper can be inserted through a tubular channel of the device to grasp tissue and draw that tissue back into the channel.

A tension member attached to the tubular member can be operated extracorporeally to bend the tubular member back on itself thereby closing the tubular channel to facilitate removal of the enclosed tissue. A flap can be positioned to extend through an opening into the tube so that upon retraction, there are no proximally facing edges which might hang on the distal edge of the trocar. The flap as well as the procedure for bending the tube back on itself provides for optimal sealing of the retrieval apparatus.

The tubular bag can be formed from transparent materials in order to facilitate viewing. In a particular embodiment the bag can be formed with a porous structure.

In one aspect, a tissue capture bag is adapted for use through a hole in a body wall and comprises a flexible tube having a wall defining an interior region extending between a first end and a second end of the tube. First portions of the first end of the tube have a first edge facing the second end of the tube. Second portions of the second end of the tube have a second edge which faces the first end of the tube. Together the first edge and the second edge define an opening into the tube. A flap extends through this opening interiorly of the first portions of the tube and exteriorly of the second portions of the tube. This flap has a fixed relationship with the first portions of the tube.

In a further aspect of the invention, a tissue capture apparatus is adapted for use in capturing and removing tissue through a hole in a body wall. The apparatus includes an elongate enclosure extending between a first end and a second end, the enclosure being sized and configured to extend through the hole in the body wall. Portions of the first end of the enclosure form an opening into the enclosure, the opening being defined by a first edge and a second edge. A flap extending through the opening distally of the elongate apparatus forms a lip to facilitate placement of the tissue into the enclosure. A coupling attaches the flap to the enclosure generally along the first edge of the opening. A tension member is coupled to the enclosure along at least a point disposed not more distally than the coupling associated with the flap. With this construction the tension member can be pulled proximally to invert the apparatus without inverting the flap so that the flap covers the second edge of the opening in order to close the opening with the tissue disposed within the enclosure.

A further aspect of the invention includes a method for removing tissue through a hole in a body wall defining a body cavity. A tissue capture apparatus is provided and includes a flexible enclosure having a channel extending longitudinally between a first end and a second end. Portions of the first end define an opening into the enclosure. A flap included in the apparatus is attached along a side of the opening and extends through the opening. The first end of the enclosure is inserted through the hole in the body wall and into the body cavity. The tissue is then placed through the opening and into the enclosure of the apparatus. This enclosure is engaged at a point proximate to the side of the opening associated with the flap. Pulling the enclosure at this point inverts the end of the enclosure with the tissue disposed within the enclosure. During this pulling step, the opening is closed by the flap.

These and other features and advantages of the invention will become more apparent with a description of preferred embodiments and reference to the associated drawings.

DESCRIPTION OF THE DRAWINGS

FIG. 6 is a side elevation view similar to FIG. 5B and illustrating the tissue drawn proximally into the bag;

FIG. 7 is a side elevation view similar to FIG. 6 and illustrating operation of a tension member to close the bag around the captured tissue;

FIG. 8 is a side elevation view similar to FIG. 7 and illustrating the capture bag in the closed state;

FIG. 9 is a side elevation view similar to FIG. 8 and illustrating removal of the bag and captured tissue in proximity of the trocar;

DESCRIPTION OF PREFERRED EMBODIMENTS AND BEST MODE OF THE INVENTION

Figure 1:
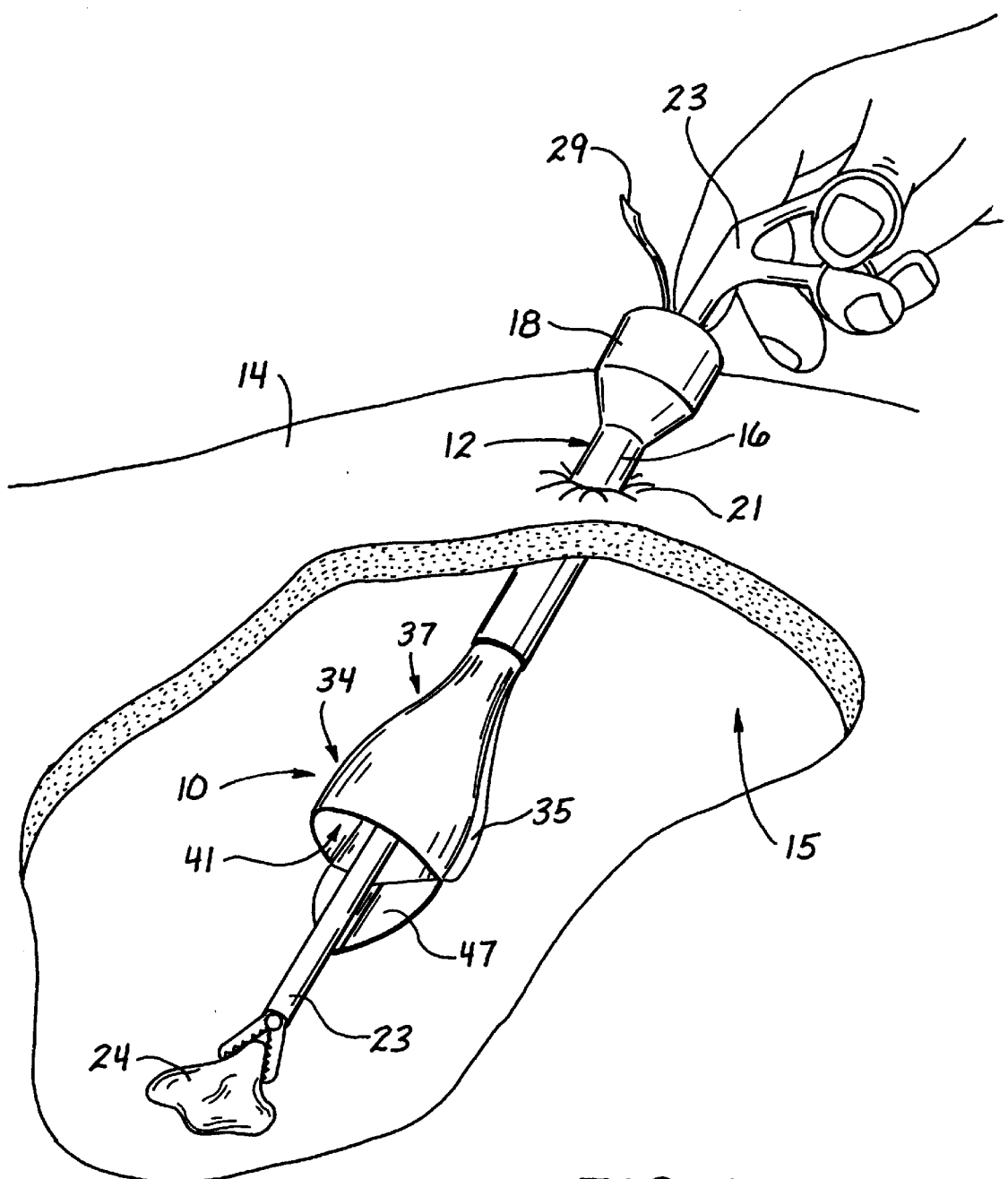
FIG. 1 is a perspective view illustrating one embodiment of the tissue capture apparatus or bag inserted through a trocar into an abdominal cavity and operatively disposed to receive tissue within the capture bag.

A tissue capture apparatus is illustrated in FIG. 1 and designated generally by the reference numeral 10. This apparatus is sized and configured for use in laparoscopic surgery where a trocar 12 functions as an access device extending across an abdominal wall 14 and into an abdominal cavity 15. As illustrated in FIG. 1, the trocar 12, which typically includes a cannula 16 and a valve housing 18, is inserted through a puncture hole or incision 21 in the abdominal wall 14. The cannula 16 and housing 18 form a working channel through which instruments, such as the tissue capture apparatus 10, can be inserted to provide extracorporeal access into the abdominal cavity 15. It will be appreciated that the tissue capture apparatus 10 can be used across any body wall, such as the abdominal wall 14, to gain access to any body cavity, such as the abdominal cavity 15. In a particular procedure, this access may be gained without the use of the trocar 12 or other supplemental access device. Also illustrated in FIG. 1 is a grasper 23 which functions in combination with the apparatus 10 to capture and remove tissue 24 from the cavity 15.

Figure 2:
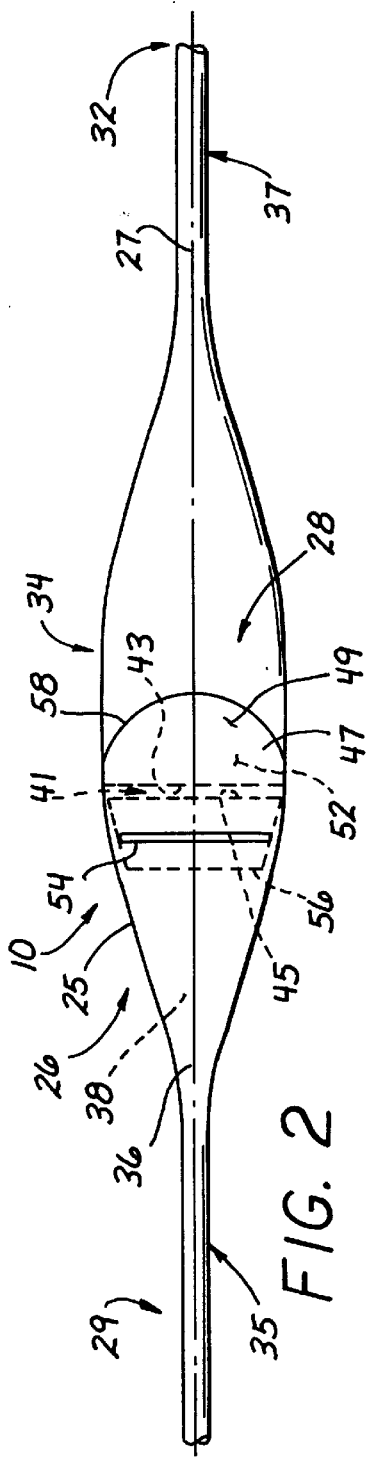
FIG. 2 is a top plan view of the bag embodiment illustrated in FIG. 1, the apparatus including a tubular enclosure having an opening and a flap extending through the opening.
Figure 3:
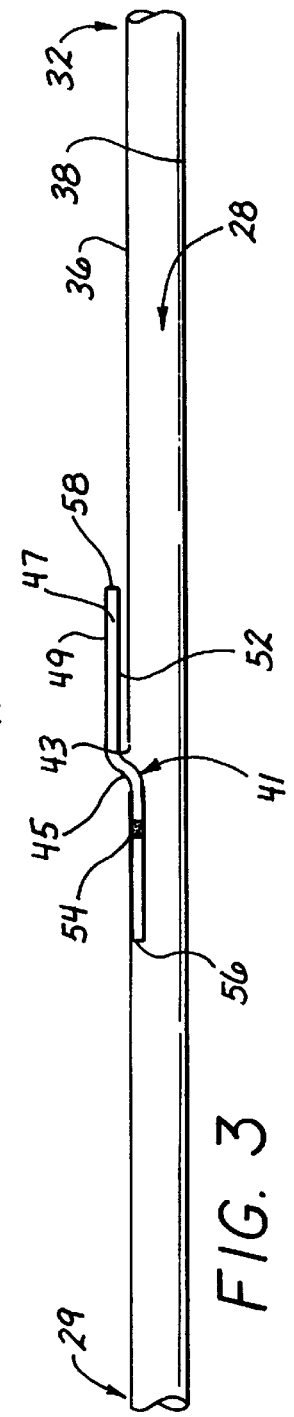
FIG. 3 is a side elevation view of the capture bag illustrated in FIG. 2.

The detail of the tissue capture apparatus 10 is perhaps best illustrated in the plan view of FIG. 2 and the side elevation view of FIG. 3. In this embodiment, the apparatus 10 includes a flexible tubular wall 25 forming a bag or enclosure 26 which extends longitudinally along an axis 27 between a first end 29 and a second end 32. This enclosure 26 forms a channel 28 along the axis 27.

In a preferred embodiment, the tissue capture apparatus 10 is enlarged at a central section 34 disposed between an end section 35 having an end 29 and an end section 37 have an end 32. In an operative state, the tubular wall 25 will be flattened slightly as illustrated in FIG. 3, so that the enclosure 26 has a first side 36 and a second side 38.

In the illustrated embodiment, the central section 34 is slit along the first side 36 to form an opening 41 into the channel 28. This opening 41 has a first side 43 which faces the first end 29 and a second side 45 which faces the second end 32. Although the opening 41 is illustrated in FIG. 2 to have some width, in a preferred embodiment, the opening 41 is formed merely as a slit which extends transverse to the axis 27 along the width of the first side, 36 but has substantially no axial dimension.

A flap 47 has a width generally equivalent of the first side 36 and extends through the opening 41. This flap 47 has an outwardly facing surface 49 and an inwardly facing surface 52. The flap 47 is attached to the first side 36 interiorly of the channel 28 typically along a line of attachment 54. With the flap 47 extending through the opening 41, the surface 49 faces the second side 41 of the opening 49 with the surface 52 facing the first side 43 of the opening 41. With this construction, the flap 47 has a first edge 56 which faces the first end 29 interiorly of the channel 28, and a second edge 58 which faces the second end 32 exteriorly of the channel 28.

Figure 4:
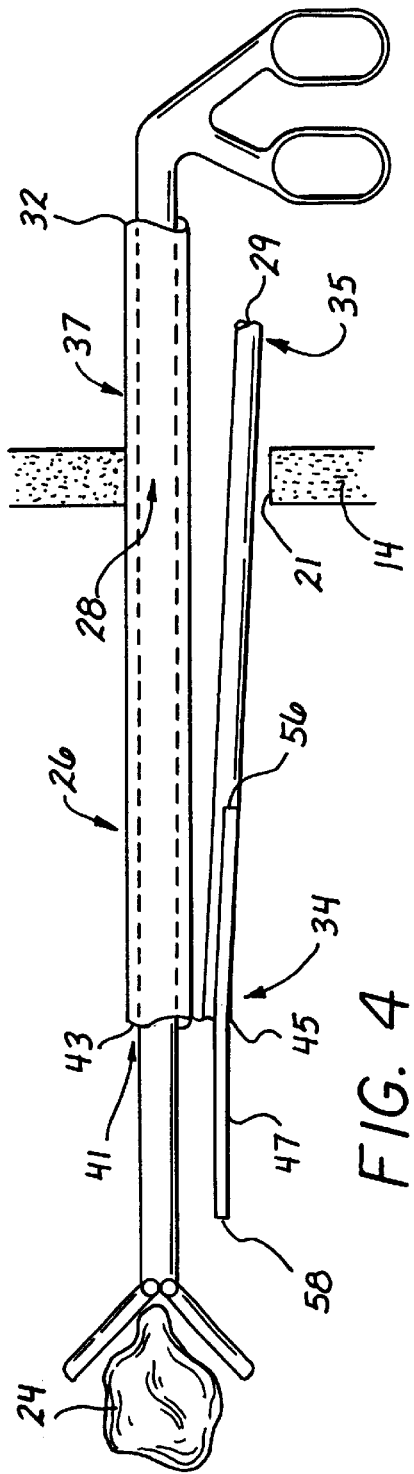
FIG. 4 is a side elevation view illustrating the capture bag operatively disposed across a body wall to facilitate grasping and retrieving of tissue from a body cavity.

When operatively disposed, the tissue capture apparatus 10 of the FIG. 1 embodiment will have a side elevation view as illustrated in FIG. 4. In this view, the end section 35 and a portion of the central section 34 up to the opening 41 is bent back on itself and positioned to extend through the incision 21 beside the end section 37. Interiorly of the cavity 15, the opening 41 faces distally with the flap 47 extending beyond the opening 41 to provide a funnel or guide for the tissue 24 entering the channel 28 of the enclosure 26.

Figure 5:
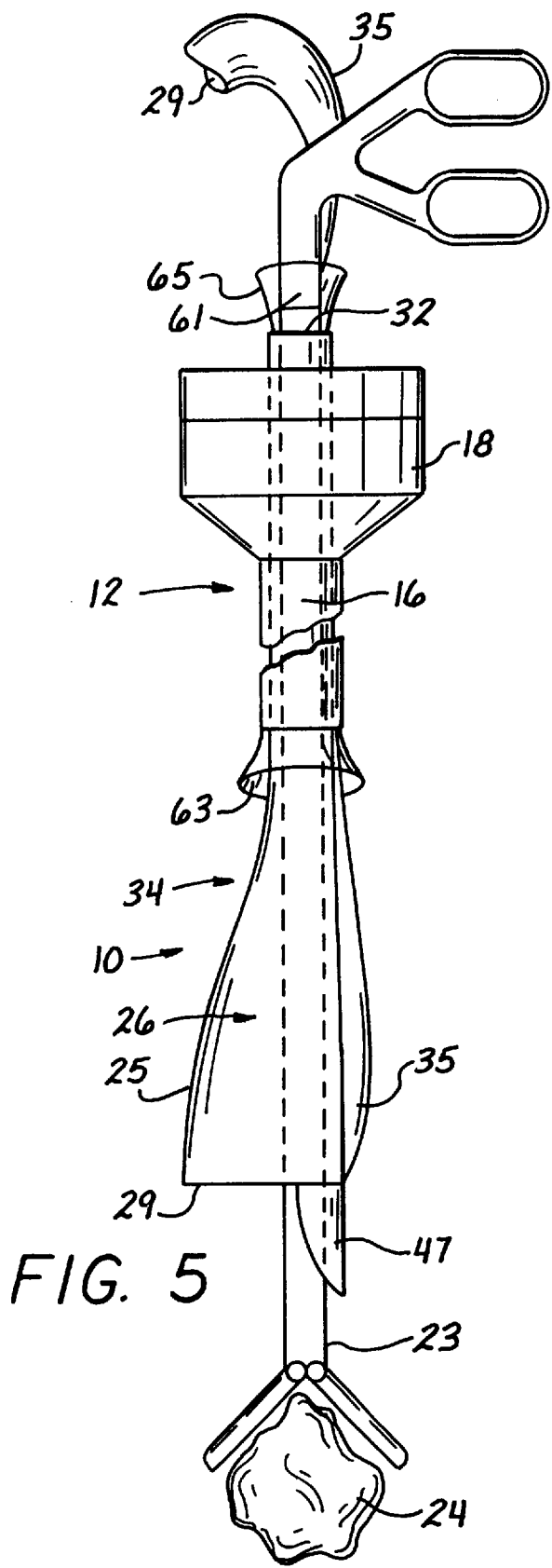
FIG. 5 is a side elevation view similar to FIG. 4 but also illustrating a trocar sleeve adapted for disposition between the capture bag and the trocar.

As illustrated in FIG. 4, the tissue capture apparatus 10 can be used without a trocar such as that designated by the reference numeral 12 in FIG. 1. As the further alternative, the trocar 12 can be provided with a sleeve 61 as illustrated in FIG. 5. The sleeve 61 has an elongate and configuration and effectively lines the interior of the cannula 16. The sleeve 61 extends to opposing ends 63 and 65 which are flared exteriorly of the trocar 12 in the preferred embodiment. It is the purpose of the sleeve 61 to provide a low friction surface within the working channel of the trocar 12 in order to facilitate insertion and removal of the tissue capture apparatus 10.

After the apparatus 10 has been operatively positioned as illustrated in FIG. 5, the grasper 23 can be inserted through the open end 32, the channel 28, and the open end 29 of the apparatus 10. In the operative position illustrated in FIG. 5, the jaws of the grasper 23 can be manipulated to engage the tissue 24.

After the tissue 24 has been engaged, the grasper 23 can be moved proximally to draw the tissue 24 through the opening 41 and into the enclosure 26 as illustrated in FIG. 6.

With the tissue 24 positioned within the enclosure 26, the apparatus 10 can be operated to capture the tissue 24, in this case by the opening 41. This is accomplished in a preferred embodiment by applying tension to the end section 35. This tension initially draws the first side 43 of the opening 41 into close proximity with the second side 45 of the opening 41 to effectively close and seal the tissue 24 within the enclosure 26. This feature of the present invention is best illustrated in FIG. 7.

After the tissue 24 has been captured and sealed within the enclosure 26, the apparatus 10 can be operated to remove the apparatus 10 together with the enclosed tissue 24 and the trocar 12, through the incision 21. This can be accomplished without removing the graspers 23, although in a preferred method the graspers 23 are first withdrawn so that the only material left in the channel 28 is the tissue 24.

As additional tension is applied to the end section 35 the line of attachment 54 is drawn proximally and the central section 34 begins to invert as illustrated in FIG. 8. Since the end section 35 is attached proximally of the opening 41, the flap 47 does not invert but rather continues to extend in the distal direction. Importantly, the edge 43 of the opening 41, which faces proximally upon inversion, is covered by the flap 47. This ensures that the edge 43 does not catch on the distal edge of the trocar 12 as the apparatus 10 is being inverted into the cannula 16. It will be noted that all of the other edges which are exposed during the inversion step face distally so that there is no possibility that any portion of the apparatus 10 will catch on the distal edge of the trocar 12. These other edges include the second side 45 of the opening 41 as well as the leading edge 58 of the flap 47.

As the end section 35 is pulled further proximally, the central section 34 is drawn even further into the cannula 16 of the trocar 12 as illustrated in FIG. 9. If the mass of the tissue 24 is relatively small, the entire tissue capture apparatus 10 may be drawn into the cannula 16. Alternatively, if the mass of the tissue 24 is large, its full retraction into the cannula 16 may not be possible. Under these circumstances, the cannula 12 can be removed followed by a small exposed portion of the apparatus 10 with the enclosed tissue 24 as illustrated in FIG. 9.

Figure 10:
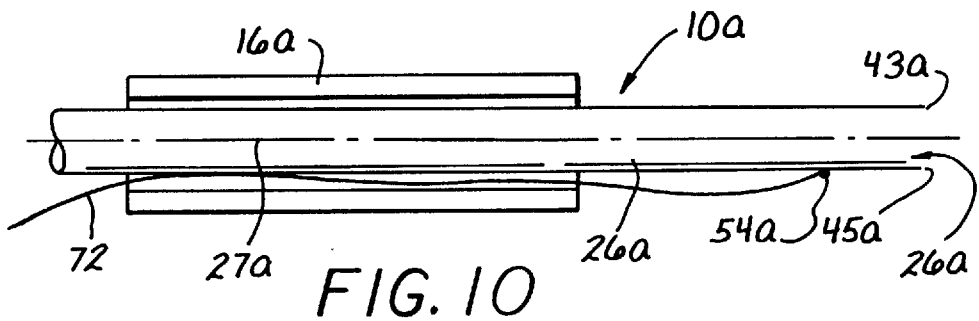
FIG. 10 is a side elevation view of a simplified embodiment of the invention including a flexible tube and tension members.
Figure 11:
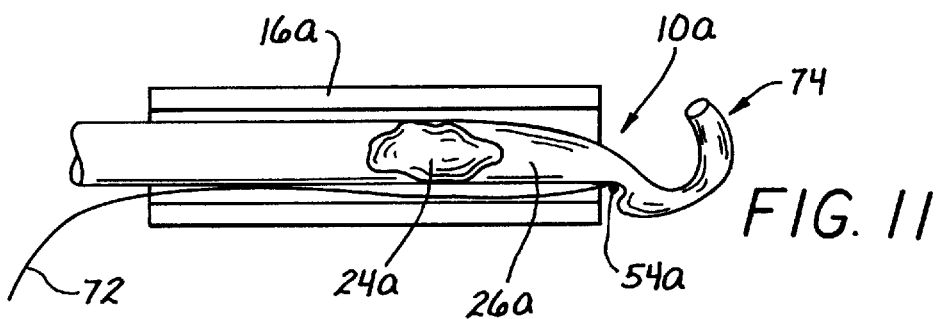
FIG. 11 is a side elevation view of the embodiment of FIG. 10 illustrating operation of the tension member to capture the tissue within the tube.

An additional embodiment of the invention is illustrated in FIGS. 10 and 11 wherein elements of structure which are similar to those previously discussed are designated with the same reference numeral followed by the lower case letter a. Thus in FIG. 10, a tissue capture apparatus 10a is disposed to extend through a cannula 16a where its tubular wall 25a forms an enclosure 26a. The opening 41a faces distally and is defined generally by a first side 43a and a second side 45a. In this case, the end section 35 which forms the tension member in the previous embodiment, is replaced by an elongate member 72 which does not necessarily have a tubular configuration. This tension member 72 is connected in the preferred embodiment proximity of the opening 41a and along a line of attachment 54a.

Inversion of this structure is best illustrated in FIG. 11 which shows a mass of tissue 24a disposed within the enclosure 26a. As the tension element 72a is drawn proximally, its line of attachment 54a is also moved in the direction of the cannula 16a. This movement of the wall 25a initially causes the opening 41 to be closed, substantially sealing the tissue 24a within the enclosure 26a. Further movement of the tension element 72 in the proximal direction causes the distal end of the wall 25a to fold back on itself as the apparatus 10a is inverted and drawn proximally toward the cannula 16a. This distal end of the wall 25a is illustrated in FIG. 11 where it is designated by the reference numeral 74.

It will be noted that in this simplified embodiment, the tissue capture apparatus 10a can be formed as a single tubular structure having the opening 41a facing distally at the distal end of the apparatus 10a. Graspers can be used in the manner previously disclosed to engage the tissue 24a and draw it proximally into the enclosure 26a. Then the enclosure 26a can be closed and sealed and the apparatus 10a inverted to draw it back toward the cannula 16a. In this withdrawn position, the apparatus 10a can be removed through the incision 21 (FIG. 1) along with the enclosed tissue 24a and the cannula 16a.

Figure 12:
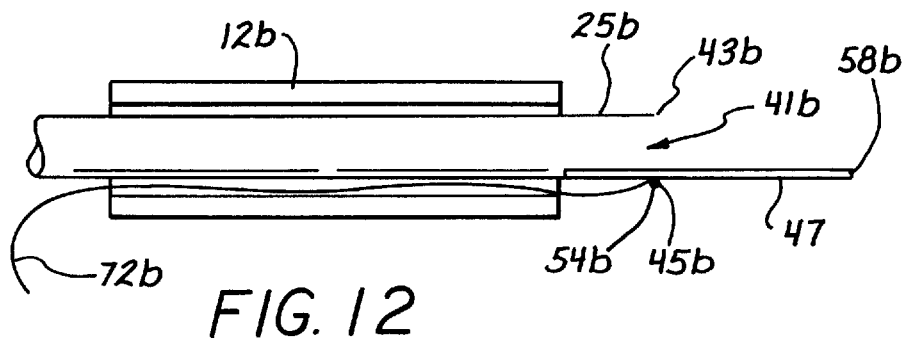
FIG. 12 is a side elevation view of an additional simplified embodiment including a flap.
Figure 13:
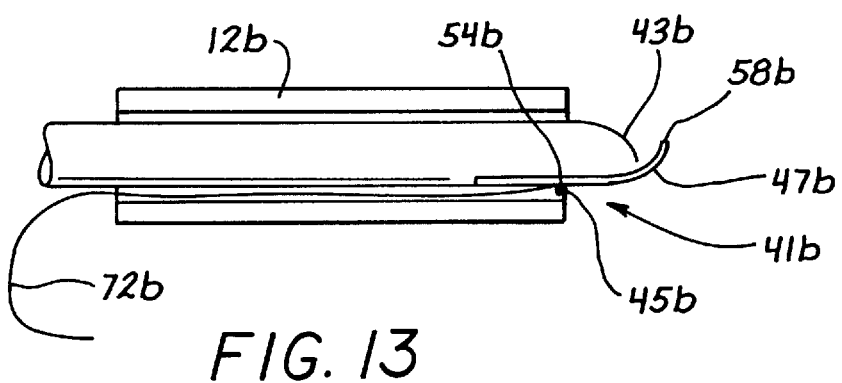
FIG. 13 is a side elevation view of the embodiment of FIG. 12 illustrating operation of the tension member to close the tube with the flap.

A further embodiment of the invention is illustrated in FIGS. 12 and 13. This embodiment combines some of the simplicity discussed with reference to FIG. 10 with other features discussed with reference to FIG. 2. One such feature relates to the flap 49b which can be attached in proximity to the side 45b of the opening 41b. Although this embodiment of the apparatus 10 is formed as a single tube, it benefits from the closure characteristics previously described with reference to FIGS. 6–9. As the tension element 72b is drawn proximally, the line of attachment 54b follows. As the edge 43b of the opening 41b inverts, it is covered by the non-inverting flap 47b to prevent any exposure of proximally facing edges which might get caught on the trocar 12b.

From a discussion of these additional embodiments of the concept, it will be apparent that the tension number 72 need not have a tubular configuration as illustrated in the embodiment of FIG. 2. Even in this embodiment where the tension member 72 is provided as an end section 35 of the tubular wall 25, it need not function as an enclosure. The advantage of the FIG. 2 embodiment is that the entire structure, except for the flap 47, can be formed from bump tubing. This configuration accommodates the enlarged central section 34 in order to facilitate withdrawal of the tissue 24 into the enclosure 26. The end section 34 is automatically formed as part of this structure and is integrally attached to the central section 34.

Where a simple tubular wall 25 is preferred, as in the embodiments of FIGS. 10–13, the tension member 72 can take generally any elongate form sufficient to engage the tubular wall 25a near its distal end. The line of attachment 54a preferably will extend transverse to the axis 27a and across substantially the entire width of the tubular wall 25a. Various shapes for the line of attachment 54a can be provided to facilitate the collapse closing, sealing and inversion of the opening 41b.

In the embodiment illustrated in FIG. 2, the tissue closure apparatus 10 is formed of polyethylene. This material seems to provide the best compromise to accommodate the functions desired for the various elements of the apparatus 10. Where these elements are not formed as a single structure, their differing functions may be further facilitated by specific materials. For example, the wall 25a forming the enclosure 26a may be formed from LDPE film which provides this wall 25a with characteristics for expansion in order to accommodate larger masses of the tissue 24a. By comparison, the tension member 72a can generally be made from any material, preferably non-expansible, which can transfer a tension force from the proximal end to the distal end of the tubular wall 25a. In a preferred embodiment, the tension element 72 is formed from HDPE film.

The tubular wall 25a can also be formed from a porous material which facilitates the removal of liquids from the tissue 24 as the apparatus 10 is drawn into the cannula 16. As illustrated in FIG. 9, operation of the tension member 72 reduces the volume of the cavity 26 thereby creating the effect of pressure on the tissue 24. This effectively removes liquids from the tissue 24 resulting in a smaller mass and facilitating removal of the tissue 24 through the incision 21 (FIG. 1).

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A tissue capture bag adapted for use through a hole in a body wall, comprising:

a flexible tube having a wall defining an interior region extending between a first end and a second end of the tube;

first portions at the first end of the tube having a first edge facing the second end of the tube;

second portions at the second end of the tube having a second edge facing the first end of the tube;

the first edge of the first portions and the second edge of the second portions defining an opening through the wall and into the interior regions of the tube between the first end and the second end of the tube; and a flap extending through the opening and being disposed interiorly of the first portions of the tube and exteriorly of the second portions of the tube, the flap having a fixed relationship with the first portions of the tube.

2. The tissue capture bag recited in claim 1 wherein:

the tube extends along an axis between the first end and the second end; and at least the second edge of the second portions extends generally transverse to the axis of the tube.

3. The tissue capture bag recited in claim 2 further comprising:

means for attaching the flap to the tube to maintain the flap in the fixed relationship with the first portions of the tube.

4. The tissue capture bag recited in claim 1 wherein:

the second edge has a length extending generally transverse to the axis to the tube;

the flap has a longitudinal dimension extending along the axis of the tube and a transverse dimension extending along the second edge of the tube; and the transverse dimension of the flap is generally equivalent to the length of the second edge of the second portions of the tube.

5. The tissue capture bag recited in claim 4 wherein the second edge is generally straight and extends generally perpendicular to the axis of the tube.

6. Tissue capture apparatus adapted for use in capturing and removing tissue through a hole in a body wall defining a body cavity, comprising:

a flexible enclosure extending between a distal end and a proximal end, the enclosure being sized and configured to extend through the hole with at least the distal end of the enclosure positioned within the body cavity;

portions of the enclosure defining a first edge and a second edge forming an opening into the enclosure;

a flap extending through the opening and distally of the enclosure to form a lip having a free end and facilitating movement of the tissue through the opening and into the enclosure;

a coupling attaching the flap to the enclosure generally along the first edge of the opening;

a tension member coupled to the enclosure at a point disposed not more distally than the coupling associated with the flap;

the tension member being operable through the hole in the body wall to invert the apparatus without inverting the flap so that the flap covers the second edge of the opening in order to close the opening with the tissue disposed within the enclosure.

7. The tissue capture apparatus recited in claim 6 wherein the tension member is integral with the elongated enclosure.

8. A method for removing tissue through a hole in a body wall defining a body cavity, comprising the steps of:

providing a tissue capture apparatus including a flexible enclosure having a channel extending longitudinally between a first end and a second end of the enclosure, with portions of the first end of the enclosure defining an opening into the enclosure, the apparatus having a flap extending through the opening and being attached along a side of the opening defining portions;

inserting the first end of the enclosure through the hole in the body wall and into the body cavity;

moving tissue through the opening in the first end of the enclosure and into the channel of the enclosure;

engaging the enclosure at a point proximate to the side of the opening defining portions;

pulling the point of the enclosure proximally to at least partially to invert the enclosure with the tissue disposed within the channel of the enclosure; and during the pulling step covering the opening with the flap.

9. The method recited in claim 8 wherein the covering step further comprises the step of:

covering the opening with the flap extending from the side of the opening defining portions toward the body cavity.

10. The method recited in claim 8 wherein the placing step further comprises the steps of:

providing an elongate grasper;

inserting the grasper through the channel of the enclosure and into the body cavity;

grasping the tissue in the body cavity;

pulling the grasped tissue into the channel of the enclosure;

disengaging the tissue within the channel of the enclosure;

removing the grasper from the channel of the enclosure.

11. The method recited in claim 10 wherein the inserting step comprises the steps of:

forming a second opening into the channel at the second end of the enclosure; and inserting the grasper through the second opening and into the channel of the enclosure.

12. The method recited in claim 8 wherein the engaging step further comprises the steps of:

providing a tension member; and coupling the tension member to the enclosure at the point proximate to the side of the opening defining portions.

13. The method recited in claim 12 wherein the pulling step includes the step of pulling the tension member beside the flexible enclosure and through the hole in the body wall to invert the enclosure with the tissue disposed within the channel of the enclosure.

14. The method recited in claim 13 wherein the coupling step further comprises the step of:

attaching the tension member to the enclosure along a line including the point, the line being generally parallel to the side of the opening.

15. A tissue capture bag adapted for use through a hole in a body wall, comprising:

a flexible tube formed of a porous material and having a wall defining an interior region extending between a first end and a second end of the tube;

first portions at the first end of the tube having a first edge facing the second end of the tube;

second portions at the second end of the tube having a second edge facing the first end of the tube;

the first edge of the first portions and the second edge of the second portions defining an opening between the first end and the second end of the tube; and a flap extending through the opening and being disposed interiorly of the first portions of the tube and exteriorly of the second portions of the tube, the flap having a fixed relationship with the first portions of the tube.

16. Tissue capture apparatus adapted for use in capturing and removing tissue through a hole in a body wall defining a body cavity, comprising:

an elongate, flexible enclosure extending between a distal end a proximal end, the enclosure being sized and configured to extend through the hole with first end positioned within the body cavity and the second end positioned outside the body cavity;

portions of the distal end defining a first edge and a second edge forming an opening into the enclosure;

a flap extending through the opening and distally of the elongate apparatus to form a lip facilitating placement of the tissue through the opening and into the enclosure;

a coupling attaching the flap to the enclosure generally along a first line extending along the first edge of the opening;

a tension member coupled to the enclosure along a second line disposed proximally of the first line; whereby the tension member can be pulled proximally through the hole in the body wall to invert the apparatus without inverting the flap so that the flap covers the second edge of the opening in order to close the opening with the tissue disposed within the enclosure.

17. Tissue capture apparatus adapted for use in capturing and removing tissue through a hole in a body wall defining a body cavity, comprising:

an elongate, flexible enclosure formed of a porous material and extending between a distal end a proximal end, the enclosure being sized and configured to extend through the hole with first end positioned within the body cavity and the second end positioned outside the body cavity;

portions of the distal end defining a first edge and a second edge forming an opening into the enclosure;

a flap extending through the opening and distally of the elongate apparatus to form a lip facilitating placement of the tissue through the opening and into the enclosure;

a coupling attaching to the enclosure generally along the first edge of the opening;

a tension member coupled to the enclosure along at least a point disposed not more distally than the coupling associated with the flap; whereby the tension member can be pulled through the hole in the body wall proximally to invert the apparatus without inverting the flap so that the flap covers the second edge of the opening in order to close the opening with the tissue disposed within the enclosure.

18. Tissue capture apparatus adapted in capturing and removing tissue through a hole in a body wall defining a body cavity, comprising:

a flexible enclosure extending between a distal end and a proximal end, the enclosure being sized and configured to extend through the hole with at least the distal end of the enclosure positioned within the body cavity;

portions of the enclosure having a first edge defining an opening into the enclosure; and a flap coupled to the enclosure and extending through the opening into the enclosure.

19. The tissue capture apparatus recited in claim 18, wherein the apparatus is moveable between a first position wherein the flap uncovers the opening, and a second position wherein the flap covers the opening.

20. The tissue capture apparatus recited in claim 19, wherein the flap in both the first and second positions extends distally.

* * * * *